(12) United States Patent
Yu

(10) Patent No.: US 12,007,377 B2
(45) Date of Patent: Jun. 11, 2024

(54) SYSTEM AND METHOD FOR BUILDING DETECTION MODEL BASED ON STANDARD VALUE TO CONFIRM SOLDERING STATUS

(71) Applicants: Inventec (Pudong) Technology Corporation, Shanghai (CN); INVENTEC CORPORATION, Taipei (TW)

(72) Inventor: Li Yu, Shanghai (CN)

(73) Assignees: Inventec (Pudong) Technology Corporation, Shanghai (CN); INVENTEC CORPORATION, Taipei (TW)

(*) Notice: Subject to any disclaimer, the term of this patent is extended or adjusted under 35 U.S.C. 154(b) by 824 days.

(21) Appl. No.: 17/013,663

(22) Filed: Sep. 7, 2020

(65) Prior Publication Data

US 2021/0072215 A1 Mar. 11, 2021

(30) Foreign Application Priority Data

Sep. 9, 2019 (CN) .................... 2019108577363.3

(51) Int. Cl.
*G01N 33/207* (2019.01)

(52) U.S. Cl.
CPC ................... *G01N 33/207* (2019.01)

(58) Field of Classification Search
CPC ............... G01N 33/207; B23K 31/125
See application file for complete search history.

(56) References Cited

U.S. PATENT DOCUMENTS

| 6,463,426 | B1* | 10/2002 | Lipson | ............... G06F 16/5854 |
| | | | | 707/E17.02 |
| 2010/0082913 | A1* | 4/2010 | Mukai | ................... H05K 3/341 |
| | | | | 711/E12.001 |
| 2019/0254173 | A1* | 8/2019 | Chang | ................. H05K 3/3442 |

\* cited by examiner

*Primary Examiner* — Manuel A Rivera Vargas
(74) *Attorney, Agent, or Firm* — IPRTOP LLC

(57) ABSTRACT

The present disclosure provides a method and a system for building a detection model based on a standard value to confirm a soldering status. The present disclosure generates the solder joint classification based on the standard value data, and uses the detection model to analyze whether the second solder joint data generated by detecting the PCB has poor soldering conditions after building the detection model based on the first solder joint data corresponding to the solder joint included in the solder joint classification, thereby achieving the technical effect of reducing the number of solder joints that are misjudged as poor soldered and shortening the time required for manual re-judgment.

8 Claims, 3 Drawing Sheets

SYSTEM AND METHOD FOR BUILDING DETECTION MODEL BASED ON STANDARD VALUE TO CONFIRM SOLDERING STATUS

CROSS REFERENCE TO RELATED APPLICATION

The present disclosure is related to and claims the benefit of priority to Chinese Patent Application No. 201910857736.3, entitled "System and Method for Building Detection Model Based on Standard Value to Confirm Soldering Status", filed with CNIPA on Sep. 9, 2019, the contents of which are incorporated herein by reference in its entirety.

BACKGROUND

Field of Disclosure

The present disclosure relates to a soldering detection system and method, in particular, to a system and method for building a detection model based on a standard value to confirm soldering status.

Description of Related Arts

At present, the most commonly used technology in the electronic assembly industry is Surface-Mount Technology (SMT), which electrically connects resistors, capacitors, transistors, integrated circuits and other electronic components to a Printed Circuit Board (PCB) by soldering. The use of surface mount technology can increase the overall processing speed of the assembly.

However, due to the miniaturization and density increasing of electronic components, the probability of poor soldering of electronic components on PCB is increased accordingly. Therefore, the detection of soldering conditions in the manufacturing process of any PCB of SMT has become a necessary part.

Solder Paste Inspection (SPI) devices can detect index data of each solder joint, such as the volume, area, height, X offset, and Y offset, and use the detected index data to determine whether the solder joint is defective. Therefore, the SPI device has always played a role in detecting the soldering quality and can find defects in the soldering quality.

However, in fact, the accuracy of the SPI device is not high enough. Half of the solder joints that are judged to be poorly soldered may be confirmed by the reviewer that there is no poor soldering. This increases the unnecessary workload of the reviewer.

In summary, it can be known that there has always been a problem of insufficient detection accuracy of the conventional SPI devices, so it is necessary to propose an improved technical means to solve this problem.

SUMMARY

In view of the problem of insufficient detection accuracy of the conventional SPI devices, the present disclosure provides a system and method for building a detection model based on a standard value to confirm a soldering status.

The system includes at least: a data collection module to collect standard value data, first solder joint data, and second solder joint data, both the first solder joint data and the standard value data correspond to a solder joint; a solder joint classification module to generate solder joint classification based on the standard value data; a model building module to build a detection model based on solder joint data corresponding to the solder joint included in the solder joint classification; a data analysis module to analyze whether the second solder joint data includes poor soldering by using the detection model.

The method includes at least: collecting standard value data and first solder joint data, both the first solder joint data and the standard value data correspond to a solder joint; generating solder joint classification based on the standard value data; building a detection model based on the first solder joint data corresponding to the solder joint included in the solder joint classification; collecting second solder joint data; and analyzing whether the second solder joint data includes poor soldering by using the detection model.

The difference between the system and method disclosed in the present disclosure and the prior art is that, the present disclosure generates the solder joint classification based on the standard value data, builds the detection model based on the first solder joint data corresponding to the solder joint included in the solder joint classification, then uses the detection model to analyze whether the second solder joint data generated by detecting the PCB has poor soldering conditions. The present disclosure solves the problem existing in the prior art, and achieves the technical effect of reducing the number of solder joints for manual re-judgment and shortens the time required for manual re-judgment.

DESCRIPTION OF REFERENCE NUMERALS

Figure 1:
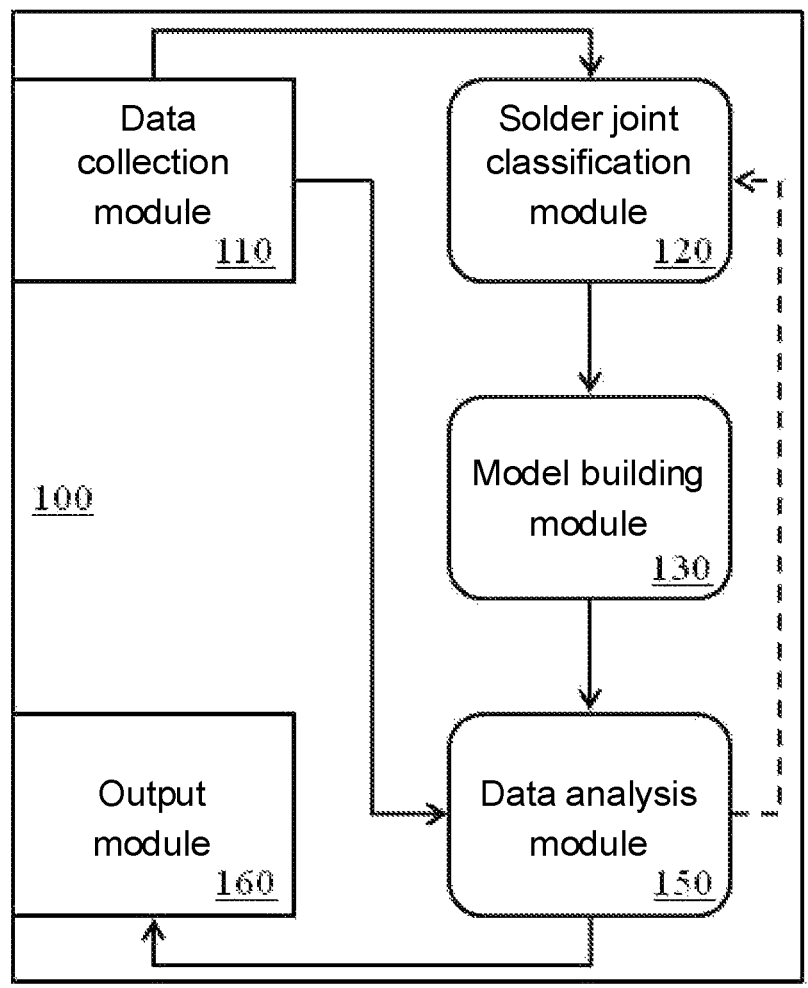
FIG. 1 shows a schematic view of a system for building a detection model based on a standard value to confirm a soldering status according to the present disclosure.

100 Computing device
110 Data collection module
120 Solder joint classification module
130 Model building module
150 Data analysis module
160 Output module
Operation 210 Collecting standard value data and first solder joint data
Operation 220 Generating solder joint classification according to the standard value data
Operation 230 Building a detection model based on the solder joint data corresponding to the solder joint included in the solder joint classification
Operation 240 Collecting second solder joint data
Operation 250 Analyzing whether the second solder joint data includes poor soldering by using the detection model
Operation 260 Outputting the second solder joint data with poor soldering
Operation 270 Adjusting the solder joint classification according to the ratio of poor soldering in the second solder joint data

DETAILED DESCRIPTION OF THE PREFERRED EMBODIMENTS

The features and embodiments of the present disclosure will be described in detail below with reference to the drawings and embodiments. The content is sufficient for anyone skilled in the art to easily and fully understand the technical means applied to solve the technical problems of the present disclosure and implement them accordingly, thereby achieving the effect that can be achieved by the present disclosure.

According to the present disclosure, a detection model can be generated based on standard value data of a solder joint or a land/pad, and the detection model can be used to analyze whether the solder joint data has poor soldering conditions. The standard value data may be the upper and lower limits of the index data of the corresponding solder joints, or may be the data of the width, height, and area of the corresponding pads. The above index data includes the volume, area, height, horizontal offset, and vertical offset of the corresponding solder joints.

The system operation of the present disclosure will be described as follows with a schematic view of a system for building a detection model based on a standard value to confirm a soldering status according to the present disclosure in FIG. 1. As shown in FIG. 1, the system of the present disclosure includes a data collection module 110, a solder joint classification module 120, a model building module 130, a data analysis module 150, and an output module 160. The system of the present disclosure can be applied to a computing device 100.

The data collection module 110 is responsible for collecting first solder joint data. The first solder joint data collected by the data collection module 110 is index data corresponding to a solder joint on a Printed Circuit Board (PCB). The PCB usually includes one or more pads, and each pad has one or more solder joints, and each solder joint corresponds to a different first solder joint data.

Generally speaking, the data collection module 110 may read the detection data of the PCB detected in the past from the storage medium of the computing device 100, and parse the detection data to obtain the first solder joint data recorded in the detection data. The data collection module 110 may be connected with an external storage device of the computing device 100 to download detection data of the PCB and obtain the first solder joint data from the detection data.

The data collection module 110 is also responsible for collecting standard value data. Each standard value data collected by the data collection module 110 may correspond to a different solder joint on the PCB, or may correspond to one or more solder joints on a different pad included in the PCB.

The data collection module 110 may obtain detection data and setting data of the same PCB from the storage medium of the computing device 100 or from the external storage device of the computing device 100, and parse the obtained setting data, thereby obtaining standard value data from the setting data.

The data collection module 110 is also responsible for collecting second solder joint data. Similar to the above, the data collection module 110 may obtain the second solder joint data from the storage medium of the computing device 100 or the external storage device of the computing device 100. The second solder joint data collected by the data collection module 110 may include, in addition to the index data corresponding to the corresponding solder joint, an image within a certain range around the solder joint (referred to as a detection image in the present disclosure). The second solder joint data may also include position information such as the coordinates or identification data of the solder joint on the pad or PCB.

The second solder joint data collected by the data collection module 110 usually includes the index data corresponding to the solder joint that a Solder Paste Inspection (SPI) device (not shown) judges to be poorly soldered after the SPI device detects all solder joints on the PCB. However, the present disclosure is not limited to this, and the second solder joint data may be index data corresponding to each solder joint on the PCB.

The solder joint classification module 120 is responsible for generating one or more solder joint classifications based on the standard value data collected by the data collection module 110. Each solder joint classification generated by the solder joint classification module 120 includes one or more solder joints. In most embodiments, different solder joint classifications will not include the same solder joint, that is, one solder joint is included in only one solder joint classification.

The solder joint classification module 120 may use a specific algorithm to classify the solder joints corresponding to the standard value data according to the upper and lower limits of the index data included in the standard value data. The algorithm used by the solder joint classification module 120 includes, but is not limited to, K-means clustering.

In some embodiments, the solder joint classification module 120 may adjust the solder joint classification according to the ratio of poor soldering in the second solder joint data analyzed by the data analysis module 150.

The model building module 130 is responsible for building a detection model based on the solder joint data corresponding to each solder joint included in each solder joint classification generated by the solder joint classification module 120. For example, the model building module 130 can randomly generate k decision trees from the solder joint data, and can use the Gini coefficient to select features. Each decision tree continuously traverses all possible segmentation points of the feature subset of the decision tree, to find the smallest feature segmentation point of the Gini coefficient to divide the data set into two subsets, until the stopping condition is met. Then the model building module 130 uses the simple voting method to take the category with the most votes as the final detection model. However, the manner in which the model building module 130 builds the detection model is not limited to the above.

The model building module 130 can divide the solder joint data into two parts. The model building module 130 can use a part of the solder joint data to train the detection model, and can use the other part of the solder joint data to predict the accuracy until the accuracy reaches a predetermined value. For example, the model building module 130 may randomly select a predetermined proportion of solder joint data from all the solder joint data to train the detection model, and use the unselected solder joint data to determine the accuracy of the detection model. If the accuracy does not reach the predetermined value, the model building module 130 may adjust the predetermined proportion, then again randomly select the adjusted predetermined proportion of solder joint data from all the solder joint data to train the detection model, and use the unselected solder joint data to determine the accuracy of the detection model. However, the present disclosure is not limited to this.

The data analysis module 150 is responsible for analyzing whether the second solder joint data collected by the data collection module 110 has a poor soldering condition using the detection model built by the model building module 130. Specifically, the data analysis module 150 can provide the second solder joint data to the detection model, so that the detection model respectively generates an analysis result corresponding to each second solder joint data. The data analysis module 150 may determine whether the corresponding second solder joint data indicates the corresponding solder joint has a poor soldering condition or not according to the analysis result generated by the detection model.

The output module 160 is responsible for outputting the second solder joint data with a poor soldering condition when the data analysis module 150 determines that the second solder joint data has a poor soldering condition. The output module 160 can display the second solder joint data with a poor soldering condition, so that the user may determine whether the solder joint corresponding to the second solder joint data is indeed poorly soldered according to the detection image included in the second solder joint data displayed by the output module 160.

In some embodiments, the output module 160 can also output the position information of the solder joint corresponding to the second solder joint data with a poor soldering condition, such as the coordinates of the solder joint on the PCB, but the present disclosure is not limited to this.

Figure 2A:
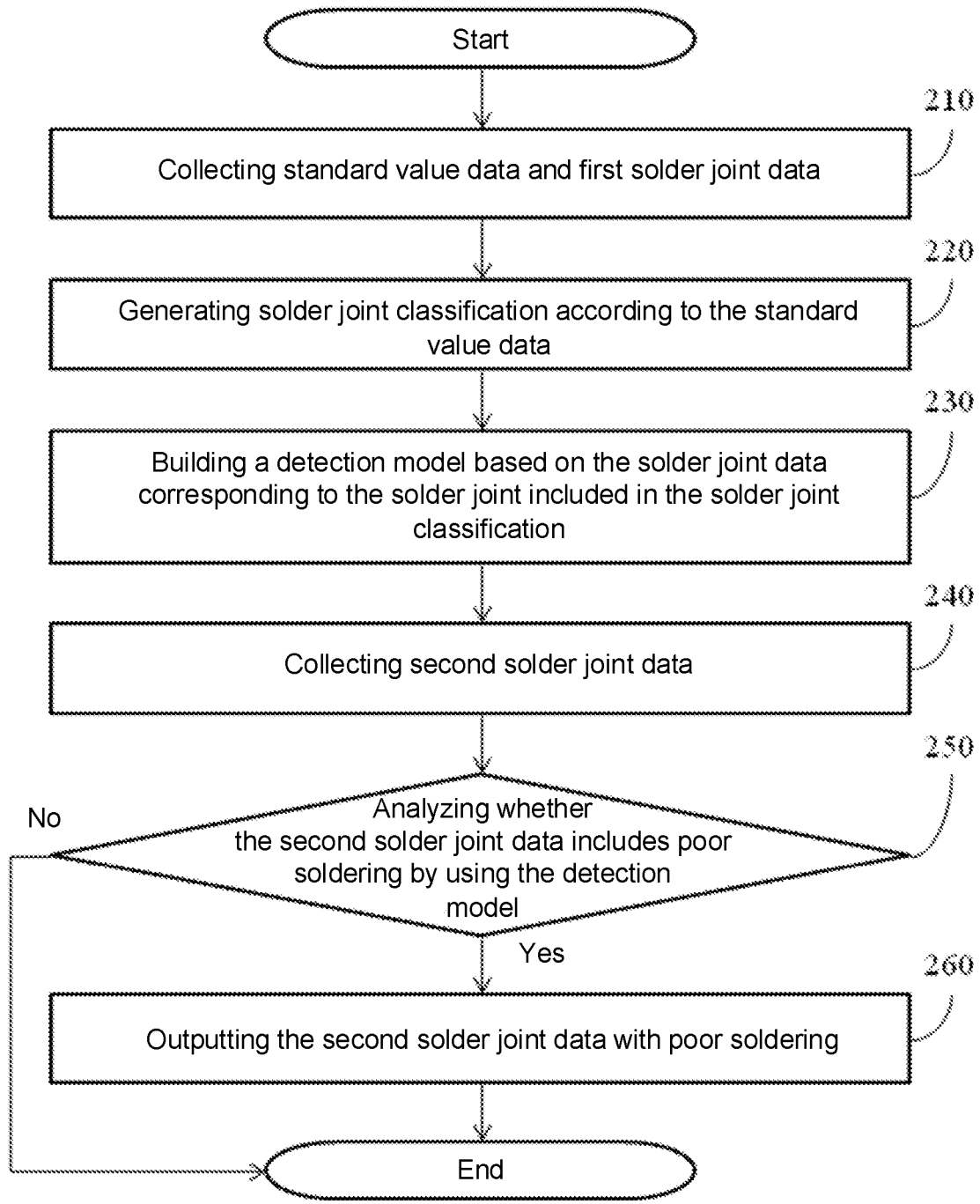
FIG. 2A shows a flowchart of a method for building a detection model based on a standard value to confirm a soldering status according to the present disclosure.

An embodiment is used to explain the operating system and method of the present disclosure. Referring to the flowchart of a method for building a detection model based on a standard value to confirm a soldering status according to the present disclosure in FIG. 2A.

First, the data collection module 110 can collect first solder joint data and standard value data corresponding to a solder joint on a PCB (operation 210). In this embodiment, it is assumed that the data collection module 110 may be connected to a server (not shown in the figure) to download the detection data and the setting data of the PCB that have been detected in the past, and parse the detection data and the setting data respectively, thereby reading out the first solder joint data and the standard value data from the detection data and the setting data.

After the data collection module 110 collects the first solder joint data and the standard value data (operation 210), the solder joint classification module 120 may generate the solder joint classification based on the standard value data collected by the data collection module 110 (operation 220), the model building module 130 may build a detection model according to the solder joint data corresponding to the solder joint included in the solder joint classification generated by the solder joint classification module 120 (operation 230). In this embodiment, it is assumed that the model building module 130 divides the solder joint data in each solder joint classification into two parts at a ratio of 3:1. The model building module 130 trains the detection model using the solder joint data of the part with a larger number, and evaluates the prediction accuracy using the solder joint data of the part with a smaller number until the accuracy reaches the predetermined value.

After the model building module 130 builds the detection model (operation 230), the data collection module 110 may collect the second solder joint data (operation 240). In this embodiment, it is assumed that the data collection module 110 is connected to a server to download a detection report generated by the SPI device for detecting the same PCB. After parsing the downloaded detection report, the solder joint data determined by the SPI device to have poor soldering is read from the detection report.

There is no sequence relationship between the building of the detection model by the model building module 130 (operation 230) and the detecting of the PCB by the SPI device to generate the detection report. That is, in the present disclosure, the model building module 130 may build the detection model before, after or at the same time as the SPI device generates the detection report, and the present disclosure is not particularly limited.

After the data collection module 110 collects the second solder joint data (operation 240), the data analysis module 150 may analyze the second solder joint data collected by the data collection module 110 using the detection model built by the model building module 130, so that the detection model analyzes whether there is poor soldering in the second solder joint data (operation 250). If not, the data analysis module 150 continues to analyze the next second solder joint data. If the data analysis module 150 determines that the analysis result output by the detection model indicates that there is poor soldering in the second solder joint data, the output module 160 may add the second solder joint data to the analysis report.

After the data analysis module 150 uses the detection model to analyze all the second solder joint data for poor soldering (operation 250), the output module 160 may store the generated analysis report in the computing device 100 or server to output the second solder joint data with poor soldering (operation 260), so that the reviewer can rejudge the solder joint corresponding to the second solder joint data according to the analysis report generated by the output module 160. In this embodiment, the output module 160 may directly display the detection image included in the second solder joint data to output the second solder joint data with poor soldering (operation 260), the user rejudges whether the solder joint corresponding to the second solder joint data is really poorly soldered according to the displayed detection image.

In this way, with the present disclosure, the probability of solder joints being misjudged as poor soldered can be reduced, and the workload of the reviewer can be reduced.

Figure 2B:
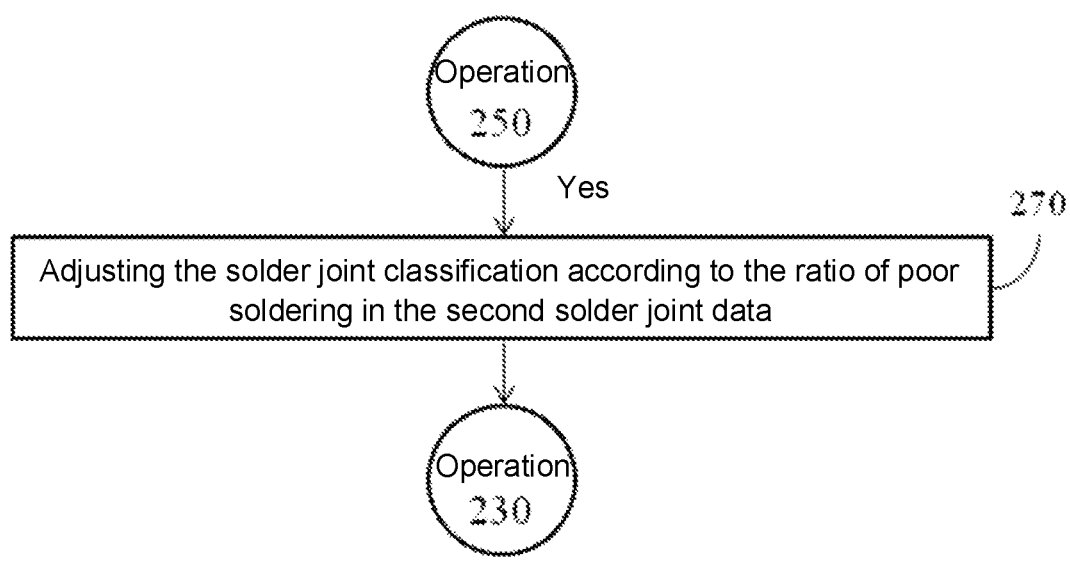
FIG. 2B shows a flowchart of a method for adjusting a solder joint classification according to a ratio of poor soldering in the present disclosure.

In addition, in the above embodiment, after the data analysis module 150 uses the detection model built by the model building module 130 to analyze whether the second solder joint data collected by the data collection module 110 has poor soldering (operation 250), the model building module 130 may adjust the solder joint classification according to the ratio of poor soldering in the second solder joint data determined by the data analysis module 150 (operation 270), as shown in the flowchart of FIG. 2B.

In summary, it can be seen that the difference between the present disclosure and the prior art is that, the present disclosure generates the solder joint classification based on the standard value data, builds the detection model based on the first solder joint data corresponding to the solder joint included in the solder joint classification, then uses the detection model to analyze whether the second solder joint data generated by detecting the PCB has poor soldering conditions. The present disclosure solves the problem of insufficient detection accuracy of the SPI device in the prior art, and achieves the technical effect of reducing the number of solder joints for manual re-judgment and shortens the time required for manual re-judgment.

Furthermore, the method for building a detection model based on a standard value to confirm a soldering status of the present disclosure can be implemented in hardware, software, or a combination of hardware and software, and can also be implemented in a computer system in a centralized manner or in a decentralized manner in which different components are spread across several interconnected computer systems.

Although the embodiments of the present disclosure have been described above, the description is not intended to limit the scope of the present disclosure. Any person having common knowledge in the art to which the present disclosure belongs can make some modifications in the form and details of the implementation without departing from the principle and scope of the present disclosure. Therefore, the protection scope of the present disclosure shall be subject to the scope defined in the attached claims.

I claim:

1. A method for building a detection model based on a standard value to confirm a soldering status, comprising at least:
   collecting a plurality of standard value data and a plurality of first solder joint data, wherein each of the plurality of first solder joint data corresponds to one of solder joints of an existing PCB layout, and each of the plurality of standard value data corresponds to at least one of the solder joints;
   generating one or more solder joint classifications according to the plurality of standard value data, wherein each of the solder joint classifications includes at least one of the solder joints;
   building a detection model based on the first solder joint data corresponding to each of the solder joints included in each of the solder joint classifications;
   collecting at least one second solder joint data of a to-be-tested PCB with the existing PCB layout, each of the at least one second solder joint data corresponds to one solder joint of the to-be-tested PCB; and
   sequentially analyzing whether each of the at least one second solder joint data includes poor soldering by using the detection model;
   wherein the collecting of the plurality of standard value data comprises:
      collecting upper and lower limits of a volume, area, height, horizontal offset, and vertical offset of each of the solder joints; or
      collecting a width, height, and area of a plurality of pads including at least one of the solder joints.

2. The method for building a detection model based on a standard value to confirm a soldering status according to claim 1, wherein after sequentially analyzing whether each of the at least one second solder joint data includes poor soldering by using the detection model, the method further comprises:
   adjusting the one or more solder joint classifications according to a ratio of poor soldering in the plurality of second solder joint data.

3. The method for building a detection model based on a standard value to confirm a soldering status according to claim 1, wherein the building of the detection model based the solder joint data corresponding to each of the solder joints included in each of the solder joint classifications further comprises:
   training the detection model by using a part of the plurality of first solder joint data, and predicting accuracy by using the other part of the plurality of first solder joint data until the accuracy reaches a predetermined value.

4. The method for building a detection model based on a standard value to confirm a soldering status according to claim 1, wherein the collecting of the at least one second solder joint data comprises:
   collecting solder joint data corresponding to a solder joint with poor soldering detected by a Solder Paste Inspection (SPI) device.

5. A system for building a detection model based on a standard value to confirm a soldering status, comprising at least:
   a data collection module to collect a plurality of standard value data and a plurality of first solder joint data, and to collect at least one second solder joint data, wherein each of the plurality of first solder joint data corresponds to one of solder joints of an existing PCB layout, and each of the plurality of standard value data corresponds to at least one of the solder joints, wherein each of the at least one second solder joint data corresponds to one solder joint of a to-be-tested PCB with the existing PCB layout;
   a solder joint classification module to generate one or more solder joint classifications according to the plurality of standard value data, wherein each of the solder joint classifications includes at least one of the solder joints;
   a model building module to build a detection model based on solder joint data corresponding to each of the solder joints included in each of the solder joint classifications; and
   a data analysis module to sequentially analyze whether each of the at least one second solder joint data includes poor soldering by using the detection model;
   wherein the plurality of standard value data comprises:
      upper and lower limits of a volume, area, height, horizontal offset, and vertical offset of each of the solder joints; or
      a width, height, and area of a plurality of pads including at least one of the solder joints.

6. The system for building a detection model based on a standard value to confirm a soldering status according to claim 5, wherein the solder joint classification module further adjusts the one or more solder joint classifications according to a ratio of poor soldering in the plurality of second solder joint data.

7. The system for building a detection model based on a standard value to confirm a soldering status according to claim 5, wherein the model building module trains the detection model by using a part of the plurality of first solder joint data, and predicts accuracy by using the other part of the plurality of first solder joint data until the accuracy reaches a predetermined value.

8. The system for building a detection model based on a standard value to confirm a soldering status according to claim 5, wherein the at least one second solder joint data comprises solder joint data corresponding to a solder joint with poor soldering detected by an SPI device.

* * * * *